US012711692B2

(12) United States Patent
Liu et al.

(10) Patent No.: US 12,711,692 B2
(45) Date of Patent: Aug. 18, 2026

(54) SYSTEMS AND METHODS FOR VOLUME RENDERING

(71) Applicant: SHANGHAI UNITED IMAGING HEALTHCARE CO., LTD., Shanghai (CN)

(72) Inventors: Xiang Liu, Shanghai (CN); Libo Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 404 days.

(21) Appl. No.: 18/332,725

(22) Filed: Jun. 10, 2023

(65) Prior Publication Data

US 2023/0410413 A1 Dec. 21, 2023

(30) Foreign Application Priority Data

Jun. 10, 2022 (CN) ......................... 202210655566.2

(51) Int. Cl.

*G06T 15/08* (2011.01)
*G06T 7/11* (2017.01)
*G16H 30/40* (2018.01)

(52) U.S. Cl.

CPC ................ *G06T 15/08* (2013.01); *G06T 7/11* (2017.01); *G16H 30/40* (2018.01)

(58) Field of Classification Search

CPC ..... G06T 15/08; G06T 2210/41; G06T 15/50; G16H 30/40; G16H 30/20; G16H 40/67

See application file for complete search history.

(56) References Cited

U.S. PATENT DOCUMENTS 5,959,631 A * 9/1999 Knittel .................... G06T 15/40 345/420
6,654,012 B1 11/2003 Lauer et al.
(Continued)

FOREIGN PATENT DOCUMENTS

CN 104167010 A 11/2014
CN 106530386 A 3/2017
(Continued)

OTHER PUBLICATIONS

Feng, Powei et al., Piecewise Tri-linear Contouring for Multi-material Volumes, Advances in Geometric Modeling and Processing, 2010, 14 pages.

*Primary Examiner* — Kent W Chang
*Assistant Examiner* — Johnny T Le
(74) *Attorney, Agent, or Firm* — METIS IP LLC

(57) ABSTRACT

The present disclosure relates to a method for image processing. The method may be implemented on a computing device having at least one storage device storing a set of instructions, and at least one processor in communication with the at least one storage device. The method may include for each stage of at least one stage of a target disease, determining a type of one or more regions of interest (ROIs) corresponding to the stage; generating a first distribution image indicating the distribution of the one or more ROIs corresponding to the stage in a subject by processing a structural image of the subject based on the type of the one or more ROIs; and generating a lesion detection result of the subject by processing a functional image of the subject based on the first distribution image corresponding to the stage.

19 Claims, 6 Drawing Sheets

100

(56) References Cited

U.S. PATENT DOCUMENTS

| | | | | |
|---|---|---|---|---|
| 7,990,378 | B2 | 8/2011 | Rabben et al. | |
| 9,224,236 | B2 | 12/2015 | Engel | |
| 10,152,821 | B2 | 12/2018 | Schneider | |
| 10,304,236 | B2 | 5/2019 | Schneider | |
| 2006/0056726 | A1* | 3/2006 | Fujiwara | G06T 15/08 382/276 |
| 2008/0024493 | A1* | 1/2008 | Bordoloi | G06T 15/08 345/423 |
| 2015/0145864 | A1* | 5/2015 | Buyanovskiy | G06T 15/08 345/426 |
| 2016/0220173 | A1* | 8/2016 | Ribnick | A61B 5/7278 |
| 2016/0307358 | A1* | 10/2016 | Suzuki | G06T 15/08 |
| 2018/0315191 | A1* | 11/2018 | Meng | G06T 3/067 |
| 2020/0143580 | A1* | 5/2020 | Seiler | G06T 11/203 |
| 2020/0388034 | A1 | 12/2020 | Meng et al. | |
| 2021/0097753 | A1* | 4/2021 | Jiang | G06T 3/60 |
| 2021/0132687 | A1* | 5/2021 | Luo | G06F 3/011 |
| 2021/0287431 | A1* | 9/2021 | Woop | G06T 15/06 |
| 2022/0092791 | A1* | 3/2022 | Dougherty | G06T 7/0012 |

FOREIGN PATENT DOCUMENTS

| | | | | |
|---|---|---|---|---|
| CN | 109147061 | A | 1/2019 | |
| CN | 110728744 | A * | 1/2020 | G06T 15/08 |
| CN | 111833427 | B * | 1/2021 | G06T 15/08 |
| CN | 113643416 | A | 11/2021 | |

* cited by examiner

SYSTEMS AND METHODS FOR VOLUME RENDERING

CROSS-REFERENCE TO RELATED APPLICATIONS

This application claims priority of Chinese Patent Application No. 202210655566.2, filed on Jun. 10, 2022, the contents of which are incorporated herein by reference.

TECHNICAL FIELD

The present disclosure generally relates to data processing, and in particular, to systems and methods for volume rendering.

BACKGROUND

A medical scanning device such as a Computed Tomography (CT) device can obtain three-dimensional volume data by scanning an object (e.g., a patient). To observe a three-dimensional structure of organs of the patient, a volume rendering operation may be performed on the three-dimensional volume data to obtain a rendered image (e.g., a two-dimensional image) on a screen. In the volume rendering operation, since voxel values of tissues of interest (e.g., the blood vessels, the heart, etc.) are similar to voxel values of adjacent tissues of the tissues of interest, parameters (e.g., a color, opacity, etc.) of the tissues of interest obtained in the volume rendering operation may be similar to the parameters of the adjacent tissues, which may result in that the tissues of interest are indistinguishable from the adjacent tissues in the rendered image.

Therefore, it is desirable to provide methods and systems for volume rendering, which may obtain a volume rendering result with improved quality and improve the efficiency of the volume rendering operation.

SUMMARY

An aspect of the present disclosure relates to a method for volume rendering, implemented on a computing device having at least one storage device storing a set of instructions, and at least one processor in communication with the at least one storage device. The method may include obtaining, based on volume data, one or more boundary meshes of one or more tissues; for each ray in a volume rendering operation, determining one or more intersections of the ray with at least one of the one or more boundary meshes; and determining, based on the one or more intersections, a volume rendering result of at least one of the one or more tissues.

Another aspect of the present disclosure relates to a system for volume rendering, including: at least one storage medium including a set of instructions; and at least one processor in communication with the at least one storage medium, wherein when executing the set of instructions, the at least one processor may be directed to cause the system to: obtain, based on volume data, one or more boundary meshes of one or more tissues; for each ray in a volume rendering operation, determine one or more intersections of the ray with at least one of the one or more boundary meshes; and determine, based on the one or more intersections, a volume rendering result of at least one of the one or more tissues.

An further aspect of the present disclosure relates to a non-transitory computer readable medium, including executable instructions that, when executed by at least one processor, direct the at least one processor to perform a method for volume rendering. The method may include: obtaining, based on volume data, one or more boundary meshes of one or more tissues; for each ray in a volume rendering operation, determining one or more intersections of the ray with at least one of the one or more boundary meshes; and determining, based on the one or more intersections, a volume rendering result of at least one of the one or more tissues.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
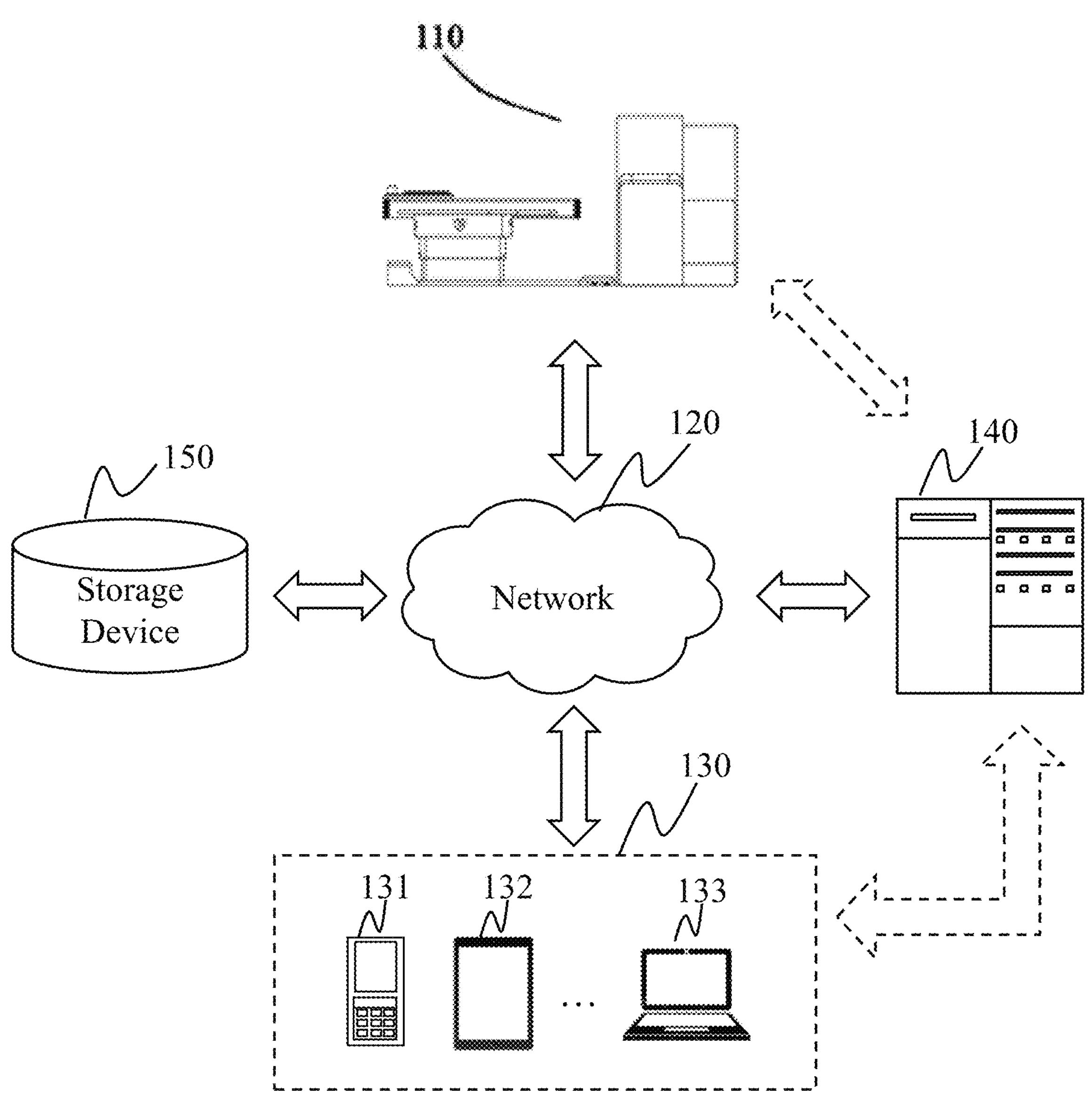
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

As used herein, the term "and/or" includes any and all combinations of one or more of the associated listed items. The term "image" in the present disclosure is used to collectively refer to imaging data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a target subject's body, since the image may indicate the actual location of a certain anatomical structure existing in or on the target subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Medical imaging device may obtain medical data by scanning a subject (e.g., a patient). For example, a Computed Tomography (CT) device may obtain volume data of the subject by scanning the subject using X-rays. The volume data may correspond to a three-dimensional (3D) image composed of a plurality of two-dimensional (2D) slice images and including a plurality of voxels. A CT value of any position in the 3D image may be obtained by performing a linear interpolation operation based on CT values of nearby voxels. In some embodiments, to observe 3D structures of organs of the subject, a volume rendering operation may be performed on the volume data based on techniques such as a ray casting or a ray tracing, and then a rendered image on a screen may be obtained. For example, in the volume rendering operation, one or more rays may be transmitted from each pixel on the rendered image on the screen. Further, for each of the one or more rays, a sampling operation may be performed on the volume data along a path of the ray passing through the volume data. In the sampling operation, a CT value of each sampling point along the path of the ray may be mapped to one or more parameters related to the volume rendering operation (e.g., an RGB value, opacity, etc.) based on information such as a window width, a window level, and/or a color table. Further, a contribution of a direct illumination or an indirect illumination at each sampling point to a brightness of the ray may be obtained based on the parameters related to the volume rendering operation and a rendering equation. The rendering equation may be used to determine, based on the parameters related to the volume rendering operation, the contribution of the direct illumination or the indirect illumination at each sampling point to the brightness of the ray. Further, the brightness of the ray may be determined by superimposing the contributions of a plurality of sampling points. The brightness may be used to represent a color of the pixel corresponding to the ray on the rendered image.

In some embodiments, the rendered image displayed on the screen may be adjusted by adjusting information such as the window width, the window level, and/or the color table. For example, by adjusting information such as the window width, the window level, and/or the color table, the opacity corresponding to tissues of interest (such as a heart, a lung, etc.) may be increased, and the opacity corresponding to tissues of no interest may be decreased. In such cases, only the tissues of interest may be displayed. As another example, the tissues of interest may be distinguished from the tissue of no interest by using different colors. In some embodiments, in the volume rendering operation, the CT values corresponding to the tissues of interest (e.g., the blood vessels, the heart, etc.) may be similar to the CT values corresponding to the tissues of no interest (e.g., tissues adjacent to the tissues of interest), which may result in that the parameters related to the volume rendering operation corresponding to the tissues of interest is similar to the parameters related to the volume rendering operation corresponding to the tissues of no interest such that the tissues of interest and the tissues of no interest cannot be distinguished when displayed.

In some embodiments, some additional information may be used to classify tissues into the tissue(s) of interest and the tissue(s) of no interest. Further, whether to display a voxel may be determined based on a classification result such that the tissue of interest may be distinguished from the tissue of no interest. For example, a tissue label of each voxel may be determined by performing, based on an image processing algorithm (e.g., an image segmentation algorithm), a segmentation operation on the volume data. In the segmentation operation, different tissue labels may correspond to different tissues. Voxels belonging to different tissues of different classifications may have different tissue labels. For each voxel in the volume data, whether to display the voxel or the tissue where the voxel is located may be determined based on the tissue label corresponding to the voxel. Optionally, voxels with different tissue labels may be displayed in different colors. In such cases, in the volume rendering operation, a tissue label of a sampling point may be determined based on the tissue label(s) of the voxel(s) at or near the sampling point, and then a display effect of the rendered image may be determined. However, due to limitations such as voxel resolution, there may be jagged edge(s) between different tissues in the rendered image. In addition, due to the volume effect, a gradient of the volume data at a boundary may be inconsistent with a boundary normal (e.g., a direction of the gradient is inconsistent with a direction of the boundary normal). In such cases, the illumination at the boundary determined based on the boundary normal may be uneven, and the boundary of the tissue may be unsmooth. In some embodiments, a smoothness of the boundary of the tissue may be improved according to a relatively high-order interpolation operation. However, the relatively high-order interpolation operation may increase the sampling times, which may affect the efficiency of the volume rendering operation.

The present disclosure may provide systems and methods for volume rendering. For volume data including one or more tissues, the methods may include obtaining, based on the volume data, one or more boundary meshes of the one or more tissues. Further, for each ray in a volume rendering operation, the methods may include determining one or more intersections of the ray with at least one of the one or more boundary meshes, and determining, based on the one or more intersections, a volume rendering result of at least one of the one or more tissues. In some embodiments, the methods may further include processing the one or more boundary meshes based on a mesh smoothing algorithm (e.g., a bilateral filter algorithm, etc.). In such cases, one or more continuous and smooth boundaries of the one or more tissues may be obtained while retaining characteristics of the one or more boundaries. Furthermore, the volume rendering operation may be performed based on boundary information of the one or more boundary meshes accurately and efficiently, which may improve continuity and smoothness of the boundaries between tissues in a volume rendering result. Moreover, the volume rendering result may not be affected by a resolution of the volume data, the volume effect, etc., thereby improving the quality of the rendered image and the efficiency of the volume rendering operation.

The following description is provided to facilitate better understanding of systems and/or methods for volume rendering. The description in connection with data relating to the imaging system described below is merely provided as an example, and not intended to limit the scope of the present disclosure. For persons having ordinary skills in the art, the systems and methods disclosed herein may be applied to any other systems (e.g., the Fenix, the metaverse) and/or devices that generate data to be rendered during operation.

FIG. 1 is a schematic diagram illustrating an exemplary imaging system according to some embodiments of the present disclosure. As illustrated, the imaging system 100 may include an imaging device 110, a network 120, a terminal device 130, a processing device 140, and a storage device 150. The components of the imaging system 100 may be connected in one or more of various ways.

The imaging device 110 may scan a subject located within its detection region and generate or acquire data relating to the subject. For example, the imaging device 110 may scan the subject and generate scan data relating to the brain of the subject. In some embodiments, the data generated or acquired by the imaging device 110 may include volume data (e.g., three-dimensional (3D) volume data, four-dimensional (4D) volume data, etc.). In some embodiments, the subject may include a biological subject and/or a non-biological subject. For example, the subject may include a specific portion of a body, such as the head, the thorax, the abdomen, or the like, or a combination thereof. As another example, the subject may be a man-made composition of organic and/or inorganic matters that are with or without life. In some embodiments, the imaging system 100 may include modules and/or components for performing imaging and/or related analysis. In some embodiments, the data relating to the subject may include projection data, scanning data, one or more images of the subject, etc.

In some embodiments, the imaging device 110 may be a medical imaging device for disease diagnostic or research purposes. The medical imaging device may include a single modality scanner and/or a multi-modality scanner. The single modality scanner may include, for example, an ultrasound scanner, an X-ray scanner, an computed tomography (CT) scanner, a magnetic resonance imaging (MRI) scanner, an ultrasonography scanner, a positron emission tomography (PET) scanner, an optical coherence tomography (OCT) scanner, an ultrasound (US) scanner, an intravascular ultrasound (IVUS) scanner, a near infrared spectroscopy (NIRS) scanner, a far infrared (FIR) scanner, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, etc. It should be noted that the scanner described above is merely provided for illustration purposes, and not intended to limit the scope of the present disclosure. The term "imaging modality" or "modality" as used herein broadly refers to an imaging method or technology that gathers, generates, processes, and/or analyzes imaging information of a target subject.

The network 120 may include any suitable network that can facilitate the exchange of information and/or data for the imaging system 100. In some embodiments, one or more components (e.g., the imaging device 110, the terminal device 130, the processing device 140, the storage device 150) of the imaging system 100 may communicate with one or more other components of the imaging system 100 via the network 120. For example, the processing device 140 may obtain volume data from the imaging device 110 via the network 120. In some embodiments, the network 120 may be any type of wired or wireless network, or a combination thereof. The network 120 may be and/or include a public network (e.g., the Internet), a private network, a wired network, a wireless network (e.g., a Wi-Fi network, etc.), a cellular network, and/or any combination thereof.

The terminal device 130 may include a mobile device 131, a tablet computer 132, a laptop computer 133, or the like, or any combination thereof. In some embodiments, the imaging device 110 and/or the processing device 140 may be remotely operated through the terminal device 130. In some embodiments, the imaging device 110 and/or the processing device 140 may be operated through the terminal device 130 via a wireless connection. In some embodiments, the terminal device 130 may receive information and/or instructions inputted by a user, and send the received information and/or instructions to the imaging device 110 or the processing device 140 via the network 120. In some embodiments, the terminal device 130 may receive data and/or information from the processing device 140. In some embodiments, the terminal device 130 may be part of the processing device 140. In some embodiments, the terminal device 130 may be omitted.

The processing device 140 may process data and/or information obtained from the imaging device 110, the terminal device 130, the storage device 150, and/or any other components associated with the imaging system 100. For example, the processing device 140 may process volume data of a subject obtained from the imaging device 110 or the storage device 150. Merely by way of example, the processing device 140 may obtain one or more boundary meshes of one or more tissues based on the volume data. For each ray in a volume rendering operation, the processing device 140 may determine one or more intersections of the ray with at least one of the one or more boundary meshes. The processing device 140 may further determine, based on the one or more intersections, a volume rendering result of at least one of the one or more tissues. Further, the processing device 140 may further control other components in the imaging system 100 based on the data, the information, and/or processing results. In some embodiments, the processing device 140 may be a single server or a server group. The server group may be centralized or distributed. In some embodiments, the processing device 140 may be local or remote. For example, the processing device 140 may access information and/or data stored in or acquired by the imaging device 110, the terminal device 130, the storage device 150, and/or any other components associated with the imaging system 100 via the network 120. As another example, the processing device 140 may be directly connected to the imaging device 110 (as illustrated by the bidirectional arrow in dashed lines connecting the processing device 140 and the imaging device 110 in FIG. 1), the terminal device 130 (as illustrated by the bidirectional arrow in dashed lines connecting the processing device 140 and the terminal device 130 in FIG. 1), and/or the storage device 150 to access stored or acquired information and/or data. In some embodiments, the processing device 140 may be implemented on a cloud platform. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the imaging device 110, the terminal device 130, and/or the processing device 140. For example, the storage device 150 may store volume data of a subject acquired by the imaging device 110. As another example, the storage device 150 may store algorithms (e.g., an algorithm for generating boundary meshes, an algorithm for managing the boundary meshes, etc.) used for volume rendering. In some embodiments, the storage device 150 may store data and/or instructions that the processing device 140 may execute or use to perform exemplary methods described in the present disclosure. For example, the storage device 150 may store instructions that the processing device 140 may execute to process the volume data acquired by the imaging device 110. In some embodiments, the storage device 150 may include a mass storage device, a removable storage device, a volatile read-and-write memory, a read-only memory (ROM), or the like, or any combination thereof. In some embodiments, the storage device 150 may be implemented on a cloud platform.

In some embodiments, the storage device 150 may be connected to the network 120 to communicate with one or more components (e.g., the imaging device 110, the processing device 140, the terminal device 130) of the imaging system 100. One or more components of the imaging system 100 may access the data or instructions stored in the storage device 150 via the network 120. In some embodiments, the storage device 150 may be directly connected to or communicate with one or more components (e.g., the imaging device 110, the processing device 140, the terminal device 130) of the Imaging system 100. In some embodiments, the storage device 150 may be part of the processing device 140.

In some embodiments, the imaging system 100 may further include one or more power supplies (not shown in FIG. 1) connected to one or more components (e.g., the imaging device 110, the processing device 140, the terminal device 130, the storage device 150) of the imaging system 100.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 2:
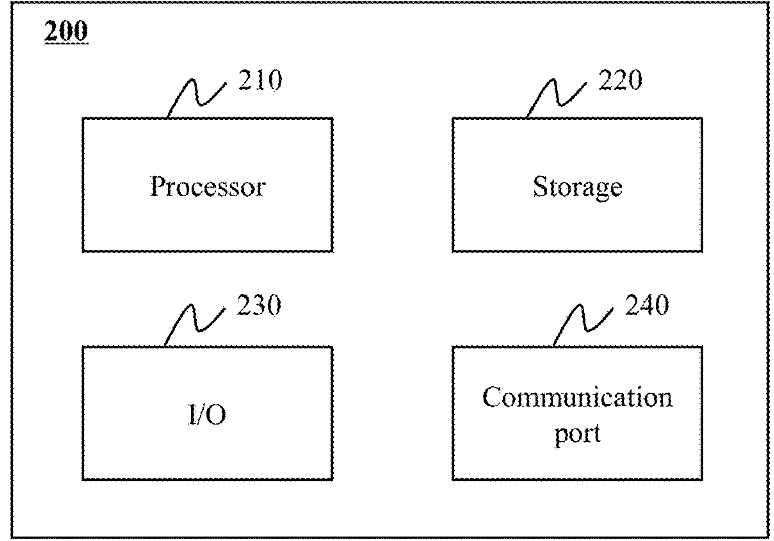
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and, when executing the instructions, cause the processing device 140 to perform functions of the processing device 140 in accordance with techniques described herein. For example, the processor 220 may obtain volume data of a subject from the imaging device 110 and generate a volume rendering result based on the volume data.

The storage 220 may store data/information obtained from the imaging device 110, the terminal device 130, the storage device 150, and/or any other component of the imaging system 100. For example, storage 220 may store a program for the processing device 140 for generating a volume rendering result based on volume data of a subject. The storage 220 may be similar to the storage device 150 described in connection with FIG. 1, and the detailed descriptions are not repeated here.

The I/O 230 may input and/or output signals, data, information, etc. In some embodiments, the I/O 230 may allow a user interaction with the processing device 140. In some embodiments, the I/O 230 may include an input device and an output device. The I/O 260 may also display images generated based on imaging data (e.g., volume data of a subject, a volume rendering result (e.g., a rendered image)). In some embodiments, the user may adjust and/or select one or more parameters relating to the volume rendering operation. For example, the user may adjust and/or select one or more parameters relating to a Marching Cube algorithm used for determining a target boundary mesh of a target tissue, one or more parameters relating to a smoothing operation, one or more parameters relating to Ray Marching algorithm used for determining intersections of a ray with one or more boundary meshes, etc. As another example, the user may select an algorithm among a plurality of algorithms for implementing a specified function. Merely by way of example, the user may select a mesh extraction algorithm among a plurality of mesh extraction algorithms (e.g., the Marching Cube algorithm, a Simple Marching Cubes (SMC) algorithm, a Cuberille algorithm, a Delaunay algorithm, etc.)

for determining a target boundary mesh. As another example, the user may select an algorithm among a plurality of algorithms for determining intersections of a ray with one or more boundary meshes (e.g., a bounding volume hierarchy (BVH) algorithm, the Ray Marching algorithm, etc.). In some embodiments, the adjustment and/or selection of the one or more parameters relating to the volume rendering operation may be transmitted to the processing device 140 as a user input. Further, the processing device 140 may receive the user input including the one or more parameters relating to the volume rendering operation and perform, based on the user input, the volume rendering operation on the volume data.

The communication port 240 may be connected to a network (e.g., the network 120) to facilitate data communications. The communication port 240 may establish connections between the processing device 140 and the imaging device 110, the terminal device 130, and/or the storage device 150.

Figure 3:
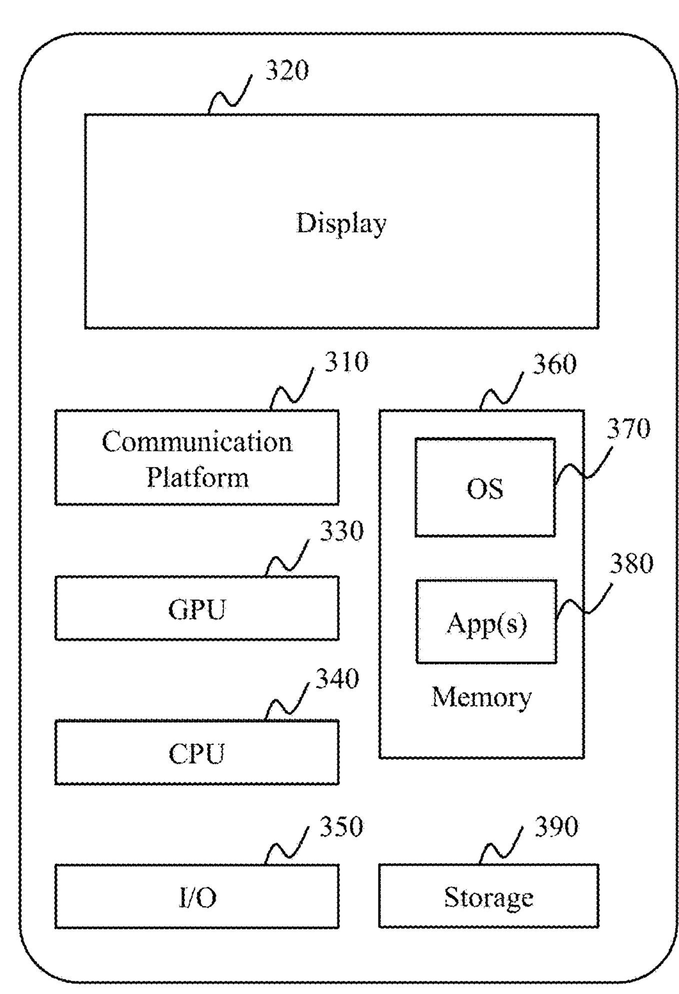
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal device 130 may be implemented on the mobile device 300. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

Figure 4:
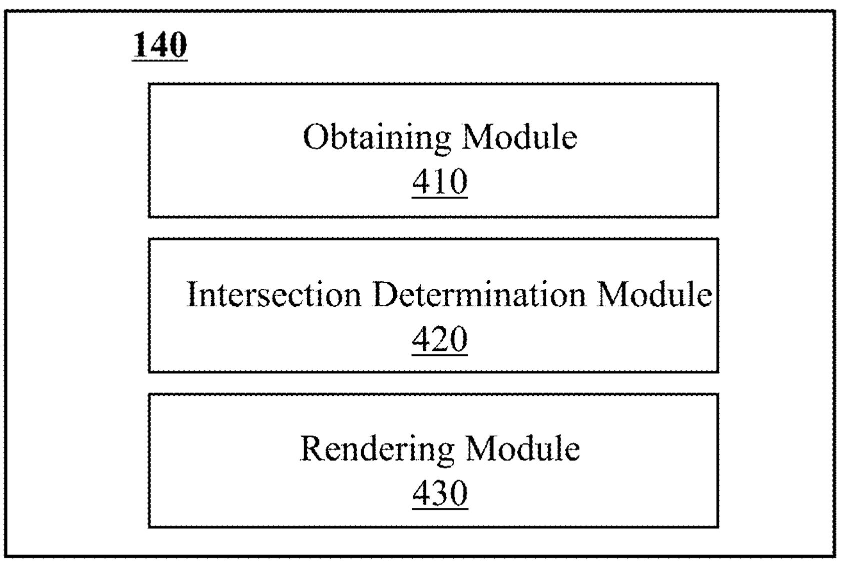
FIG. 4 is a block diagram illustrating an exemplary processing device according to some embodiments of the present disclosure.

FIG. 4 is a block diagram illustrating an exemplary processing device according to some embodiments of the present disclosure. As illustrated in FIG. 4, the processing device 140 may include an obtaining module 410, an intersection determination module 420, and a rendering module 430.

The obtaining module 410 may be configured to obtain, based on volume data, one or more boundary meshes of one or more tissues. In some embodiments, to obtain, based on volume data, one or more boundary meshes of one or more tissues, the obtaining module 410 may be configured to determine a tissue label for each voxel by performing a segmentation operation on the volume data, and determine, based on the tissue label of the each voxel, a target boundary mesh, among the one or more boundary meshes, of a target tissue corresponding to the tissue label. For example, the obtaining module 410 may perform, based on one or more tissue labels of the one or more tissues, a binarization operation on the volume data, and determine, based on at least one of a Marching Cube algorithm, a Simple Marching Cubes algorithm, a Cuberille algorithm, or a Delaunay algorithm, the target boundary mesh of the target tissue corresponding to the tissue label. In some embodiments, the obtaining module 410 may be configured further to perform a smoothing operation on the at least one of the one or more boundary meshes.

The intersection determination module 420 may be configured to, for each ray in a volume rendering operation, determine one or more intersections of the ray with at least one of the one or more boundary meshes. In some embodiments, the at least one of the one or more boundary meshes may include a plurality of mesh patches. To determine one or more intersections of the ray with at least one of the one or more boundary meshes, the intersection determination module 420 may be configured to traverse the plurality of mesh patches to determine one or more intersections of the ray with the plurality of mesh patches as the one or more intersections of the ray with the at least one of the one or more boundary meshes. For example, the intersection determination module 420 may be configured to manage, based on a bounding volume hierarchy (BVH) algorithm, the at least one of the one or more boundary meshes. One or more parent nodes and one or more leaf nodes are configured in the BVH algorithm, each of the one or more parent nodes may correspond to a bounding box, and each of the one or more leaf nodes may correspond to one or more mesh patches of the plurality of mesh patches. For each parent node of the one or more parent nodes, the intersection determination module 420 may determine whether the ray intersects with the parent node, in response to determining that the ray intersects with the parent node, the intersection determination module 420 may determine one or more intersections of the ray with one or more leaf nodes corresponding to the parent node as the one or more intersections of the ray with the plurality of mesh patches, or in response to determining that the ray does not intersect with the parent node, the intersection determination module 420 may skip the parent node and the one or more leaf nodes corresponding to the parent node.

The rendering module 430 may be configured to determine, based on the one or more intersections, a volume rendering result of at least one of the one or more tissues. In some embodiments, to determine, based on the one or more intersections, a volume rendering result of at least one of the one or more tissues, the rendering module 430 may be configured to, for the each ray in the volume rendering operation, divide, based on the one or more intersections, the ray into a plurality of segments. Further, the rendering module 430 may be configured to determine a tissue label of each segment in the plurality of segments. Further, the rendering module 430 may be configured to generate, based on the tissue label of each segment in the plurality of segments, the volume rendering result of the tissue. In some embodiments, to generate, based on the tissue label of each segment in the plurality of segments, the volume rendering result of the tissue, the rendering module 430 may be configured to determine a plurality of sampling points along the ray. Further, for each sampling point of the plurality of sampling points, the rendering module 430 may be configured to determine, based on the tissue label of each segment in the plurality of segments, a tissue label of the sampling point, and determine, based on the tissue labels of the plurality of sampling points, the volume rendering result of the tissue. For example, the rendering module 430 may determine whether each of the tissue labels of the plurality of sampling points is visible. Further, for each sampling point of the plurality of sampling points, in response to determining that the tissue label of the sampling point is invisible, the rendering module 430 may skip a segment where the sampling point is located and proceed to a next segment; or in response to determining that the tissue label of the sampling point is visible, the rendering module 430 may determine, based on one or more rendering parameters corresponding to the tissue label of the sampling point, a contribution of the sampling point to a brightness of the ray. Further, the rendering module 430 may determine, based on a plurality of contributions of the plurality of sampling points, the brightness of the ray.

In some embodiments, the rendering module 430 may be configured to determine the volume rendering result based on an user input. For example, the rendering module 430 receive a user input including one or more parameters relating to the volume rendering operation, and perform, based on the user input, volume rendering operation on the volume data to generate the volume rendering result.

It should be noted that the above descriptions of the processing device 140 and the modules are provided for the purposes of illustration, and not intended to limit the scope of the present disclosure. For persons having ordinary skills in the art, various modifications and changes in the forms and details of the application of the above method and system may occur without departing from the principles of the present disclosure. For example, the obtaining module 410, the intersection determination module 420, and the rendering module 430 may be different modules in one system, or one module that may realize the functions of the two or more modules. As another example, the processing device 140 may further include a display module configured to display a volume rendering result. However, those variations and modifications also fall within the scope of the present disclosure.

Figure 5:
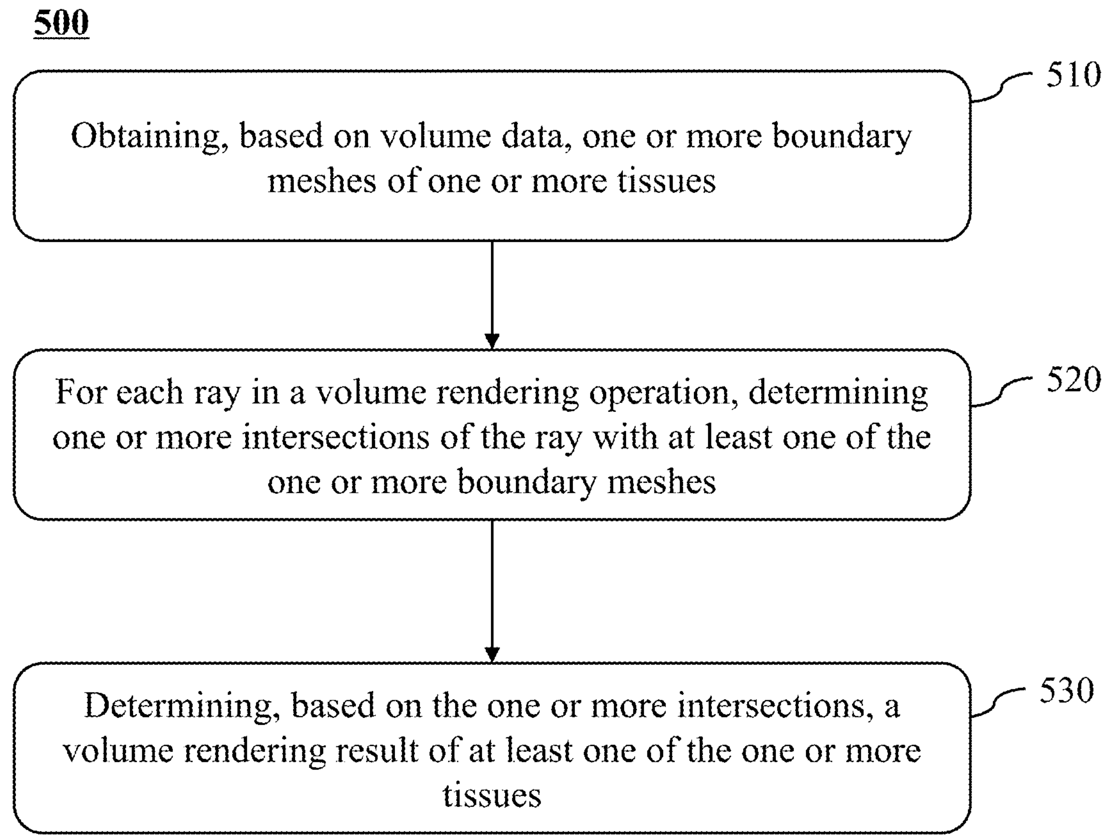
FIG. 5 is a flowchart illustrating an exemplary process for determining a volume rendering result according to some embodiments of the present disclosure.

FIG. 5 is a flowchart illustrating an exemplary process for determining a volume rendering result according to some embodiments of the present disclosure. In some embodiments, the process 500 may be implemented by an imaging system (e.g., the imaging system 100). In some embodiments, the imaging system may be implemented by software and/or hardware. In some embodiments, at least part of process 500 may be performed by the processing device 140 (implemented in, for example, the computing device 200 shown in FIG. 2). For example, the process 500 may be stored in a storage device (e.g., the storage device 150, the storage 220) in the form of instructions (e.g., an application), and invoked and/or executed by the processing device 140 (e.g., the processor 210 illustrated in FIG. 2, the one or more modules illustrated in FIG. 4).

In 510, the processing device 140 (e.g., the obtaining module 410) may obtain, based on volume data, one or more boundary meshes of one or more tissues.

In some embodiments, the volume data may be acquired based on an interaction between a subject (e.g., a human body) and a medium provided or detected by an imaging device (e.g., the imaging device 110 illustrated in FIG. 1) during a medical scanning process. Exemplary imaging devices may include an MR scanning device, a CT scanning device, an X-ray scanning device, an ultrasound scanning device, a PET scanning device, a DR scanning device, or the like, or any combination thereof. In some embodiments, the subject may include a patient, a man-made object, etc. In some embodiments, the subject may include one or more tissues of a patient. As used herein, a tissue refers to a specific portion, organ, and/or biological tissue of the patient. For example, the tissue may include a head, a brain, a neck, a body, a shoulder, an arm, a thorax, a cardiac, a stomach, a blood vessel, a soft tissue, a knee, feet, or the like, or any combination thereof. Correspondingly, the volume data generated by the imaging device may include volume data of the one or more tissues. In some embodiments, the volume data may include 3D volume data, 4D volume data, or the like, or any combination thereof. For example, the volume data may include 3D volume data composed of an image sequence including a plurality of image frames. Each image frame may be acquired by performing a scan on the subject using the imaging device. In some embodiments, the volume data may include a plurality of voxels. Each of the plurality of voxels may correspond to a voxel value (e.g., a CT value).

In some embodiments, the volume data may be obtained from the imaging device directly. In some embodiments, the volume data may be retrieved from a storage device (e.g., the storage device 150) disclosed elsewhere in the present disclosure. For example, a database may be configured in the storage device 150 for storing the volume data. The volume data generated by the imaging device 110 may be transferred to the storage device 150 and stored in the database. The processing device 140 may obtain the volume data from the database.

In some embodiments, in order to obtain, based on the volume data, the one or more boundary meshes of one or more tissues, the processing device 140 may determine a tissue label for each voxel by performing a segmentation operation on the volume data. For example, a tissue to which the each voxel in the volume data belongs and a tissue label of the each voxel (or the tissue) may be determined by performing, based on an image segmentation algorithm, a segmentation operation on the volume data. In some embodiments, different tissues may correspond to different tissue labels. Further, the processing device 140 may determine, based on the tissue label of the each voxel, a target boundary mesh (among the one or more boundary meshes) of a target tissue corresponding to the tissue label. For example, the processing device 140 may perform, based on one or more tissue labels of the one or more tissues, a binarization operation on the volume data, and determine, based on a result of the binarization operation, the target boundary mesh of the target tissue. Merely by way of example, in the binarization operation, for each tissue in the one or more tissues or for each tissue label in the one or more tissue labels, binarized volume data (also referred to as the "result of the binarization operation") may be obtained by specifying the voxel value corresponding to the tissue as 1 based on the tissue label of the tissue and specifying the voxel values corresponding to other tissues as 0. Then the target boundary mesh of the target tissue may be determined based on the binarized volume data using a mesh generation algorithm. In such cases, the one or more boundary meshes of the one or more tissues may be obtained. In some embodiments, after determining the target boundary mesh of the target tissue, a smoothed boundary mesh may be obtained by performing a smoothing operation on the target boundary mesh. More descriptions regarding determining the one or more boundary meshes of the one or more tissues may be found elsewhere in the present disclosure. See, e.g., FIG. 6 and relevant descriptions thereof.

In some embodiments, by determining the one or more boundary meshes of the one or more tissues based on a result of the segmentation operation and further performing the smoothing operation on the one or more boundary meshes, more continuous and smoother boundary meshes may be obtained while retaining boundary characteristics between tissues. In such cases, the continuity and smoothness of the boundaries of the one or more tissues in the volume rendering result may be improved, and the volume rendering result may not be affected by the resolution of the volume data, thereby improving the quality of the volume rendering result and the efficiency of the volume rendering operation. Moreover, in a process for determining the brightness of the ray based on the one or more boundary meshes, a mesh normal of a boundary mesh may be used as a normal of a sampling point near the boundary mesh, which may reduce the problems such as uneven illumination at the boundary and insufficient smoothness of the boundary of the tissue in the rendered image caused by an inconsistency between the gradient of the volume data and the boundary normal, thereby improving the quality of the rendered image.

In 520, for each ray in the volume rendering operation, the processing device 140 (e.g., the intersection determination module 420) may determine one or more intersections of the ray with at least one of the one or more boundary meshes.

In some embodiments, a rendered image on the screen may be obtained by performing, based on a volume rendering algorithm, the volume rendering operation on the 3D volume data. The rendered image may include a 2D image, a 3D image, or the like. Exemplary volume rendering algorithms may include a ray casting algorithm, a ray tracing algorithm, or the like. In the volume rendering operation, a ray may be transmitted from a viewpoint (or a camera position) and pass through each pixel on the screen. Further, a plurality of sampling points may be determined along a path of the ray passing through the volume data. Further, a brightness of the pixel corresponding to the ray may be determined by performing, based on the plurality of sampling points, a sampling operation on the volume data.

In some embodiments, for each ray in the volume rendering operation, one or more intersections of the ray with at least one of the one or more boundary meshes may be determined. In some embodiments, a boundary mesh of each tissue may include a plurality of mesh patches. In such cases, the one or more intersections of the ray with at least one of the one or more boundary meshes may be one or more intersections of the ray with the plurality of mesh patches of at least one of the one or more boundary meshes. In some embodiments, to determine the one or more intersections of the ray with at least one of the one or more boundary meshes, the processing device 140 may traverse the plurality of mesh patches to determine one or more intersections of the ray with the plurality of mesh patches as the one or more intersections of the ray with the at least one of the one or more boundary meshes. For example, when traversing the plurality of mesh patches to determine one or more intersections of the ray with the plurality of mesh patches as the one or more intersections of the ray with the at least one of the one or more boundary meshes, the processing device 140 may manage the one or more boundary meshes based on a Bounding Volume Hierarchy (BVH) algorithm. A plurality of parent nodes and one or more leaf nodes may be configured in the BVH algorithm, each parent node may correspond to a bounding box, and each of the one or more leaf nodes may correspond to one or more mesh patches of the plurality of mesh patches. For each ray in the volume rendering operation, the processing device 140 may determine whether the ray intersects with the parent node. If the ray intersects with the parent node, the processing device 140 may further determine intersections of the ray with the corresponding leaf nodes of the parent node. If the ray does not intersect with the parent node, the processing device 140 may skip the parent node and the corresponding leaf nodes. In some embodiments, a ray may pass through a plurality of tissues in the volume data. Correspondingly, the ray may intersect with the boundary meshes of the plurality of tissues at one or more intersections. In some embodiments, to determine the one or more intersections of the ray with at least one of the one or more boundary meshes, the processing device 140 may transmit the one or more boundary meshes to a graphic processing unit (e.g., the GPU 330 shown in FIG. 3) in communication with the processing device 140. Further, the graphic processing unit may determine, based on a hardware acceleration operation, the one or more intersections of the ray with at least one of the one or more boundary meshes. Further, the graphic processing unit may transmit the one or more intersections of the ray with at least one of the one or more boundary meshes to the processing device 140. More descriptions regarding determining the intersections of the ray with the at least one of the one or more boundary meshes may be found in elsewhere of the present disclosure. See, e.g., FIG. 7 and relevant descriptions thereof.

In some embodiments, the BVH algorithm is used to manage the one or more boundary meshes of the one or more tissues such that when determining the one or more intersections of the ray with at least one of the one or more boundary meshes, it is not necessary to determine whether there is an intersection between the ray and each mesh patch, which may reduce redundant calculations when the ray does not intersect with the mesh patch, thereby reducing the computational complexity and improving the computational speed of determining the one or more intersections of the ray with at least one of the one or more boundary meshes.

In 530, the processing device 140 (e.g., the rendering module 430) may determine, based on the one or more intersections, a volume rendering result of at least one of the one or more tissues.

In some embodiments, to determine the volume rendering result of at least one of the one or more tissues, for the each ray in the volume rendering operation, the processing device 140 may divide, based on the one or more intersections, the ray into a plurality of segments. Further, the processing device 140 may determine a tissue label of each segment in the plurality of segments. For example, the plurality of mesh patches corresponding to each tissue may have a tissue label of the tissue. The tissue label of a mesh patch in the plurality of mesh patches that intersects with the ray may be determined as the tissue label of the intersection between the ray and the mesh patch. In such cases, the ray may be divided into a plurality of segments based on the one or more intersections, and the tissue label of the intersection corresponding to each segment may be determined as the tissue label of the segment. Further, the processing device 140 may generate, based on the tissue label of each segment in the plurality of segments, the volume rendering result of the tissue. For example, the processing device 140 may determine a plurality of sampling points along the ray. Merely by way of example, in a volume rendering operation based on a ray casting algorithm, the sampling points may be stepped sampling points along the ray. As another example, in a volume rendering operation based on a ray tracing algorithm, the sampling points may be randomly sampled along the ray. Further, for each sampling point of the plurality of sampling points, the processing device 140 may determine, based on the tissue label of each segment in the plurality of segments, a tissue label of the sampling point. Further, the processing device 140 may determine, based on the tissue labels of the plurality of sampling points, the volume rendering result of the tissue. More descriptions regarding determining the volume rendering result may be found elsewhere in the present disclosure. See, e.g., FIG. 8 and relevant descriptions thereof.

It should be noted that the above description for the process 500 is merely provided for the purposes of illustration, and not intended to limit the scope of the present disclosure. For persons having ordinary skills in the art, multiple variations and modifications may be made under the teachings of the present disclosure. In some embodiments, the operations of the process 500 are not sequential. In some embodiments, the process 500 may include one or more additional operations, or one or more operations of the process 500 may be omitted. For example, the process 500 may also include operations for smoothing the one or more boundary meshes of the one or more tissues. As another example, the process 500 may also include an operation for displaying the volume rendering result based on the brightness of each ray.

Figure 6:
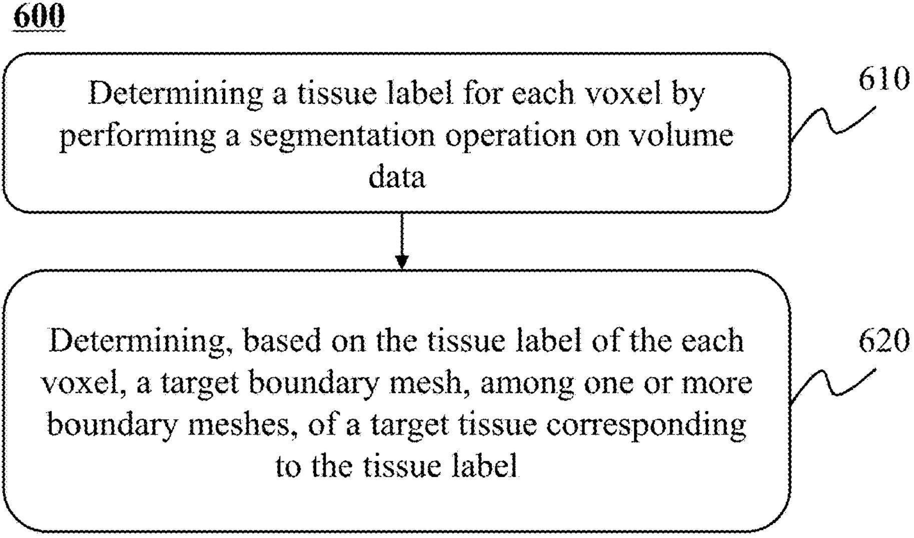
FIG. 6 is a flowchart illustrating an exemplary process for determining one or more boundary meshes of one or more tissues according to some embodiments of the present disclosure.
Figure 6:

FIG. 6 is a flowchart illustrating an exemplary process for determining one or more boundary meshes of one or more tissues according to some embodiments of the present disclosure. In some embodiments, the process 600 may be implemented by an imaging system (e.g., the imaging system 100). In some embodiments, operation 510 in the process 500 may be performed according to the process 600.

In 610, the processing device 140 may determine a tissue label for each voxel by performing a segmentation operation on the volume data.

In some embodiments, the volume data may include one or more tissues. The processing device 140 may determine a tissue corresponding to each voxel by performing a segmentation operation on the volume data. For example, the processing device 140 may determine the tissue corresponding to each voxel by performing, based on an image segmentation algorithm, the segmentation operation on the volume data. Exemplary image segmentation algorithms may include a graph theory-based image segmentation algorithm, a pixel clustering-based image segmentation algorithm, a semantic segmentation algorithm, or the like.

In some embodiments, a result of the segmentation operation performed on the volume data may include one or more tissues in the volume data and one or more voxels corresponding to each of the one or more tissues. The processing device 140 may determine a tissue label for each tissue or each voxel in the one or more tissues. In some embodiments, the tissue label may indicate which tissue a current voxel belongs to, and the tissue labels corresponding to different tissues may be different. For example, a tissue label of the heart may be a, a tissue label of the left lung may be b, and a tissue label of the right lung may be c, or the like. In some embodiments, the tissue labels may be represented by numbers. In some embodiments, the tissue label of each tissue may be automatically generated during the segmentation operation performed on the volume data. For example, the processing device 140 may automatically determine the tissue label of each voxel when determining, by performing the segmentation operation on the volume data based on the image segmentation algorithm, the corresponding tissue for each voxel.

In 620, the processing device 140 may determine, based on the tissue label of the each voxel, a target boundary mesh, among the one or more boundary meshes, of a target tissue corresponding to the tissue label.

A boundary mesh may refer to a mesh for representing a boundary of a tissue. For example, each tissue may have a boundary. The boundary may be an interface (e.g., an isosurface) surrounding the tissue. The interface may be represented by a mesh, i.e., the boundary mesh. In some embodiments, the boundary mesh may indicate a result of segmenting different tissues. For each tissue in the volume data, a corresponding boundary mesh may be determined. In some embodiments, the boundary mesh may include a plurality of mesh patches. Merely by way of example, a mesh patch may be a triangular mesh patch, and a plurality of triangular mesh patches may be interconnected to form a complete boundary mesh of the tissue.

In some embodiments, for each tissue label in the one or more tissue labels, the processing device 140 may determine a boundary mesh corresponding to the tissue label. The tissue corresponding to a current tissue label may be referred to as a target tissue, and the boundary mesh of the target tissue corresponding to the tissue label may be referred to as a target boundary mesh. In such cases, the processing device 140 may determine one or more boundary meshes of the one or more tissues. In some embodiments, a user may determine or select one or more target boundary meses to be generated. For example, the processing device 140 may display a selection interface and/or an input interface to the user through a user-interface (e.g., the I/O 230 shown in FIG. 2). On the selection interface and/or an input interface, the one or more tissues in the volume data obtained based on the segmentation operation may be displayed to the user. Merely by way of example, the one or more tissues in the volume data may be displayed in form of one or more names in a list, one or more images of the one or more tissues, etc. The user may select or input one or more target tissues in the one or more tissues on the selection interface and/or an input interface. Further, the processing device 140 may generate target boundary mesh(es) of the one or more target tissues based on the selection and/or the input of the user. In such cases, the processing device 140 may selectively generate boundary mesh(es) of a portion of the one or more tissues in the volume data based on user input, which may simplify a process for determining the one or more boundary meshes and improve the efficiency of determining the one or more boundary meshes.

In some embodiments, in order to determine, based on the tissue label of the each voxel, the target boundary mesh corresponding to the tissue label, the processing device 140 may perform, based on one or more tissue labels of the one or more tissues, a binarization operation on the volume data.

In some embodiments, for each tissue in the one or more tissues or for each tissue label in the one or more tissue labels obtained in the segmentation operation, the processing device 140 may perform a binarization operation on the volume data based on the tissue label of the tissue.

In the binarization operation, for each tissue label in the one or more tissue labels, a label of each voxel in the tissue may be determined as a first value, and a label of each voxel in other tissues may be determined as a second value. The first value may be different from the second value. For example, for a tissue with the tissue label of a, a label of each voxel in the tissue may be determined as 1, and a label of each voxel in other tissues (such as tissues b, c, etc.) may be determined as 0. As another example, for a tissue with the tissue label of b, the label of each voxel in the tissue may be determined as 1, and a label of each voxel in other tissues (such as tissues a, c, etc.) may be determined as 0. In such cases, the tissue label of each tissue may correspond to a result of the binarization operation. In some embodiments, the result of the binarization operation may indicate whether the tissue is visible in a following processing. For example, in a mesh extraction operation for determining the one or more boundary meshes of the one or more tissues, the first value may indicate that the tissue with the first value is visible in the mesh extraction operation, and the second value may indicate that the tissue with the second value is invisible in the mesh extraction operation. In some embodiments, the binarization operation may be performed on the volume data based on a binarization algorithm. Exemplary binarization algorithms may include a bimodal algorithm, a P-parameter algorithm, an iterative algorithm, an Otsu binarization algorithm, or the like.

Further, the processing device 140 may determine, based on a result of the binarization operation, the target boundary mesh corresponding to the tissue label.

In some embodiments, the target boundary mesh of the target tissue may be determined based on a mesh extraction algorithm. Exemplary mesh extraction algorithms may include a Marching Cube algorithm, a Simple Marching Cubes algorithm, a Cuberille algorithm, a Delaunay algorithm, etc. In some embodiments, a user may select one of the exemplary mesh extraction algorithms through a user interface. Then the processing device 140 may determine the target boundary mesh corresponding to the tissue label based on the selected mesh extraction algorithm. In some embodiments, the target boundary mesh of the target tissue corresponding to the tissue label may be determined based on a Marching Cube algorithm. Based on the Marching Cube algorithm, the processing device 140 may determine whether a tissue is visible based on the result of the binarization operation and extract a boundary mesh of a visible tissue as the target boundary mesh of the target tissue. In some embodiments, the processing device 140 may also determine whether the tissue is visible based on information such as a window width and/or a window level, and extract the boundary mesh of the tissue based on the window width and/or the window level using a mesh extraction algorithm. Optionally or additionally, the processing device 140 may extract the boundary mesh of the tissue based on both the window width, the window level, and the result of the binarization operation using the mesh extraction algorithm. In some embodiments, the processing device 140 may extract the target boundary mesh of the target tissue corresponding to the tissue label based on the result of the binarization operation corresponding to each tissue label. In such cases, the one or more boundary meshes of the one or more tissues may be obtained. In some embodiments, the target boundary mesh of the target tissue may have a tissue label corresponding to the target tissue.

In some embodiments, the processing device 140 may perform a smoothing operation on at least one of the one or more boundary meshes. In the smoothing operation, a continuous and smooth boundary mesh may be obtained by adjusting parameters related to the boundary mesh. Merely by way of example, the boundary mesh may include a plurality of triangular mesh patches, and the parameters related to the boundary mesh may include vertex parameters of the plurality of triangular mesh patches. In the smoothing operation, the vertex parameters of the plurality of triangular mesh patches may be adjusted to make a smooth transition between different triangular mesh patches such that a continuous and smooth boundary mesh may be obtained. In some embodiments, the smoothing operation may be performed on at least one of the one or more boundary meshes based on a mesh smoothing algorithm. For example, the processing device 140 may perform the smoothing operation on the at least one of the one or more boundary meshes using a bilateral filter algorithm.

According to some embodiments of the present disclosure, the result of segmenting different tissues may be extracted using the one or more boundary meshes based on the tissue label of each tissue, and the one or more boundary meshes may be used in the volume rendering operation. In addition, according to the smoothing operation performed on at least one of the one or more boundary meshes, more continuous and smoother boundary meshes may be obtained while retaining boundary characteristics between tissues. In the volume rendering operation, the boundary meshes after the smoothing operation may provide accurate tissue boundary information and improve the continuity and smoothness of the boundaries of the one or more tissues in the volume rendering result. In such cases, the volume rendering result may not be affected by the resolution of the volume data, which may improve the quality of the volume rendering result and the efficiency of the volume rendering operation.

It should be noted that the above description for the process 600 is merely provided for the purposes of illustration, and not intended to limit the scope of the present disclosure. For persons having ordinary skills in the art, multiple variations and modifications may be made under the teachings of the present disclosure. In some embodiments, the operations of the process 600 are not sequential. In some embodiments, the process 600 may include one or more additional operations, or one or more operations of the process 600 may be omitted. In some embodiments, at least two operations in the process 600 may be incorporated into an operation for implementation or one operation in the process 600 may be divided into two operations for implementation. For example, the operation 610 may be divided into two operations, in one operation, a segmentation operation may be performed on the volume data to determine the tissue corresponding to each voxel, and in the other operation, the tissue label for each tissue may be determined based on a result of the segmentation operation. As another example, the operation 620 may be divided into two operations, in one operation, the binarization operation may be performed, based on one or more tissue labels of the one or more tissues, on the volume data, and in the other operation, the target boundary mesh corresponding to the tissue label may be determined based on a result of the binarization operation. As a further example, the process 600 may further include an operation of smoothing at least one of the one or more boundary meshes. As a further example, in the operation 610, a trained neural network model may be used to segment the volume data. As a further example, the operation 620 may be omitted, and a trained neural network model may be used to extract the boundary mesh from the segmented volume data. Optionally or additionally, a same neural network model may be used for segmenting the volume data and extracting the boundary mesh.

Figure 7:
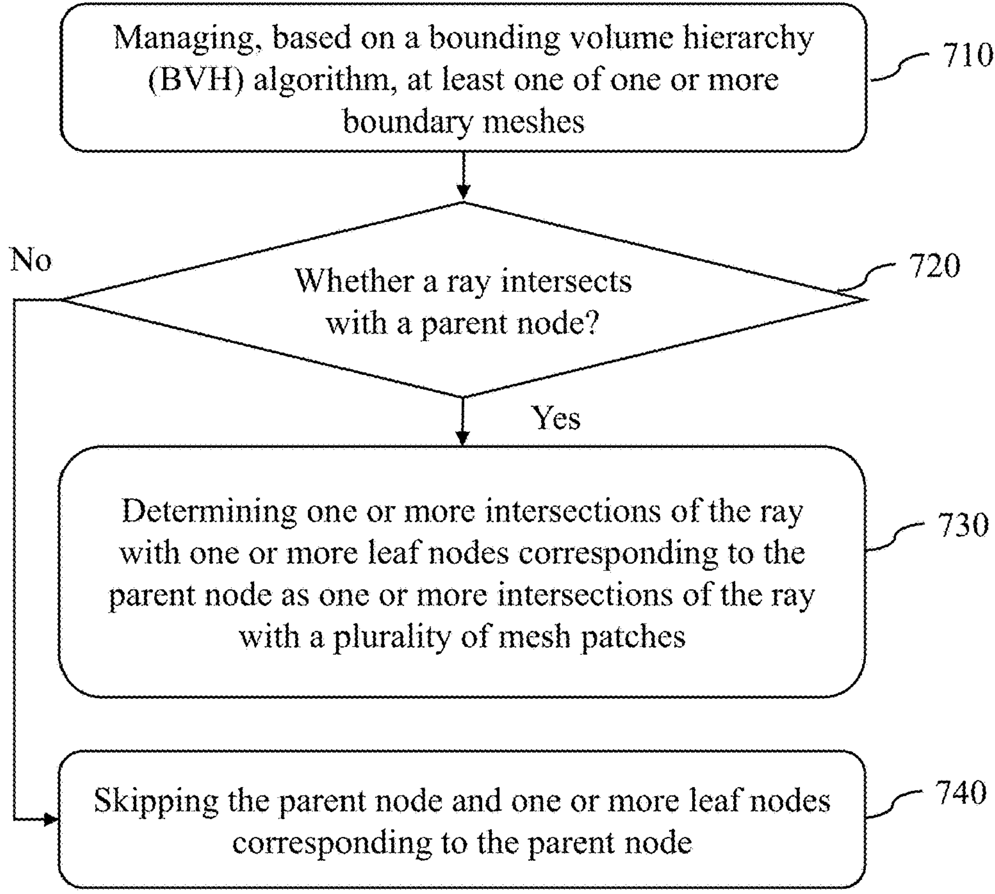
FIG. 7 is a flowchart illustrating an exemplary process for determining one or more intersections of a ray with at least one of one or more boundary meshes according to some embodiments of the present disclosure.

FIG. 7 is a flowchart illustrating an exemplary process for determining one or more intersections of a ray with at least one of one or more boundary meshes according to some embodiments of the present disclosure. In some embodiments, the process 700 may be implemented by an imaging system (e.g., the imaging system 100). In some embodiments, operation 520 in the process 500 may be performed according to the process 700. In some embodiments, the process 700 may be performed for each ray in a volume rendering operation.

In 710, the processing device 140 may manage, based on a bounding volume hierarchy (BVH) algorithm, at least one of the one or more boundary meshes.

In some embodiments, a tree structure for managing the one or more boundary meshes of the one or more tissues in the volume data, may be constructed based on the BVH algorithm. For example, the at least one of the one or more boundary meshes may include a plurality of mesh patches. The tree structure may include one or more parent nodes and one or more leaf nodes, each of the one or more parent nodes may correspond to a bounding box, and each of the one or more leaf nodes may correspond to one or more mesh patches of the plurality of mesh patches. In some embodiments, each bounding box may represent a 3D spatial range in the volume data and bound one or more mesh patches. In such cases, based on the BVH algorithm, a plurality of bounding boxes may be determined, and each bounding box may bound one or more mesh patches such that the at least one of the one or more boundary meshes may be managed based on the plurality of bounding boxes. In some embodiments, at least a portion of the plurality of bounding boxes may overlap. For example, the mesh patches in two or more bounding boxes may partially overlap. In some embodiments, the tree structure may include a plurality of layers of nodes. For example, each parent node may correspond to a bounding box, and each bounding box may bound a plurality of lower-layer bounding boxes. Further, each lower-layer bounding box may bound one or more mesh patches. In some embodiments, the processing device 140 may manage at least one of the one or more boundary meshes. In some embodiments, the processing device 140 may manage all of the one or more boundary meshes. In some embodiments, the processing device 140 may manage at least one of the one or more boundary meshes based on one or more other algorithms. Exemplary algorithms for managing the at least one of the one or more boundary meshes may include an Oct Tree algorithm, a KD (k-dimensional) Tree algorithm, etc.

In 720, for each parent node of the one or more parent nodes, the processing device 140 may determine whether the ray intersects with the parent node.

In some embodiments, for each ray in the volume rendering operation, the processing device 140 may determine whether the ray intersects with each parent node of the one or more parent nodes. For example, the processing device 140 may determine whether the ray intersects with the parent node based on the BVH algorithm. As another example, the processing device 140 may determine whether the ray intersects with the parent node by determining a spatial position relationship between a path of the ray in the volume data and the bounding box corresponding to the parent node. If at least a portion of the ray passes through a 3D spatial range corresponding to the bounding box, the processing device 140 may determine that the ray intersects with the parent node. In some embodiments, for each ray in the volume rendering operation, the processing device 140 may traverse the one or more parent nodes in the BVH algorithm to determine whether the ray intersects with each parent node.

In 730, in response to determining that the ray intersects with the parent node, the processing device 140 may determine one or more intersections of the ray with one or more leaf nodes corresponding to the parent node as the one or more intersections of the ray with the plurality of mesh patches.

In 740, in response to determining that the ray does not intersect with the parent node, the processing device 140 may skip the parent node and the one or more leaf nodes corresponding to the parent node.

In some embodiments, if the ray intersects with the parent node, the ray may intersect with one or more mesh patches in the bounding box. In such cases, in response to determining that the ray intersects with the parent node, the processing device 140 may determine the intersections of the ray with the corresponding leaf nodes of the parent node. For example, the processing device 140 may determine the intersections of the ray with the corresponding leaf nodes of the parent node by traversing each leaf node of the parent node. In response to determining that the ray does not intersect with the parent node, the ray may not intersect with the one or more mesh patches in the bounding box. In such cases, if the ray does not intersect with the parent node, the parent node and the corresponding leaf nodes of the parent node may be skipped. Further, the processing device 140 may determine whether the ray intersects with a next parent node until all of the one or more parent nodes in the BVH algorithm are traversed. In some embodiments, a ray may pass through a plurality of tissues in the volume data. Correspondingly, a ray may intersect with the boundary meshes of the plurality of tissues at one or more intersections. In some embodiments, a ray may intersect with the boundary mesh of the tissue at different positions along the ray and have one or more intersections with the boundary mesh.

According to some embodiments of the present disclosure, the one or more boundary meshes of the one or more tissues may be managed using the BVH algorithm. When determining the intersections of the ray with at least one of the one or more boundary meshes, the processing device 140 may determine whether the ray intersects with the parent node. If the ray intersects with the parent node, the processing device 140 may further determine the intersections of the ray with the leaf nodes corresponding to the parent node. If the ray does not intersect with the parent node, the parent node and the corresponding leaf nodes may be skipped. In such cases, when determining the intersections of the ray with at least one of the one or more boundary meshes, the processing device 140 may not determine whether the ray intersects with each of the plurality of mesh patches in the at least one of the one or more boundary meshes, which may avoid redundant calculations when the ray does not intersect with the plurality of mesh patches, thereby reducing the computational complexity of determining the intersections, and improving the computational speed of determining the intersections.

In some embodiments, to determine the intersections of the ray with at least one of the one or more boundary meshes, a distance field of at least one of the one or more boundary meshes may be constructed. For any point in the volume data, the distance field may include a shortest distance from the point to the at least one of the one or more boundary meshes. In such cases, for any point on the ray, the shortest distance from the point to the at least one of the one or more boundary meshes may be determined based on the distance field. Further, the intersections of the ray with the at least one of the one or more boundary meshes may be determined based on a Ray Marching algorithm. For example, in the Ray Marching algorithm, a plurality of sampling points may be determined by marching along, according to a certain step, the ray. Based on the distance field, a shortest distance from each sampling point of the plurality of sampling points on the ray to the at least one of the one or more boundary meshes may be determined. Further, whether the ray intersects the at least one of the one or more boundary meshes may be determined based on the shortest distance of each sampling point along the ray, and the intersections of the ray with the at least one of the one or more boundary meshes may be determined when the ray intersects the at least one of the one or more boundary meshes. In such cases, whether the ray intersects the at least one of the one or more boundary meshes may be determined based on the shortest distance of each sampling point along the ray, which may reduce redundant calculations of determining the intersections and improving the speed of determining the intersections.

It should be noted that the above description for the process 700 is merely provided for the purposes of illustration, and not intended to limit the scope of the present disclosure. For persons having ordinary skills in the art, multiple variations and modifications may be made under the teachings of the present disclosure. In some embodiments, the operations of the process 700 are not sequential. In some embodiments, the process 700 may include one or more additional operations, or one or more operations of the process 700 may be omitted. In some embodiments, at least two operations in the process 700 may be incorporated into an operation for implementation or one operation in the process 700 may be divided into two operations.

Figure 8:
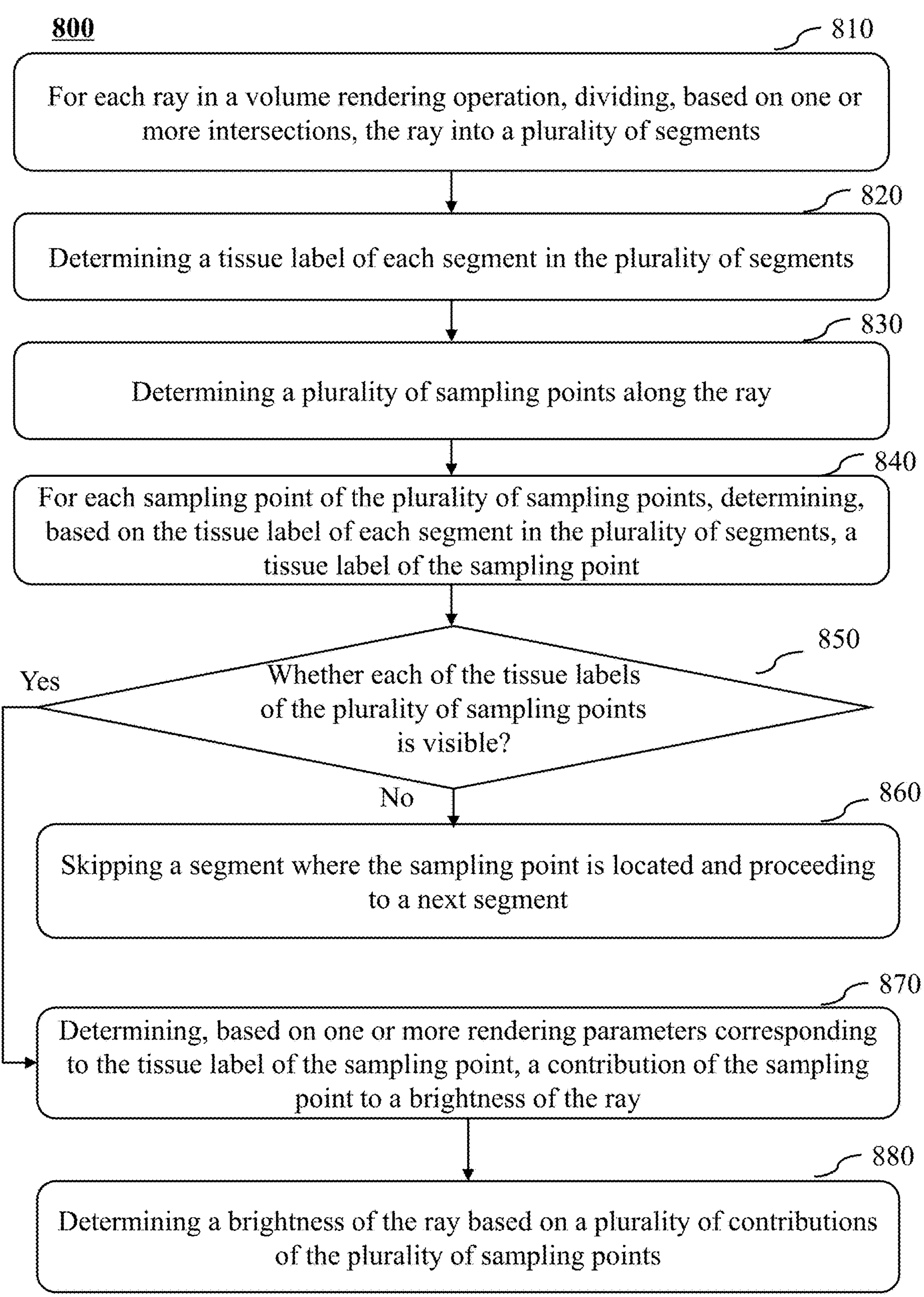
FIG. 8 is a flowchart illustrating an exemplary process for determining a volume rendering result according to some embodiments of the present disclosure.

FIG. 8 is a flowchart illustrating an exemplary process for determining a volume rendering result according to some embodiments of the present disclosure. In some embodiments, the process 800 may be implemented by an imaging system (e.g., the imaging system 100). In some embodiments, operation 530 in the process 500 may be performed according to the process 800. In some embodiments, the process 800 may be performed for each ray in a volume rendering operation.

In 810, for the each ray in the volume rendering operation, the processing device 140 may divide, based on the one or more intersections, the ray into a plurality of segments.

In some embodiments, when passing through the volume data, the ray may intersect with at least one of the one or more boundary meshes of the one or more tissues at one or more intersections. The processing device 140 may divide, based on the one or more intersections, the ray into a plurality of segments. For example, a segment may be determined based on two adjacent intersections.

In 820, the processing device 140 may determine a tissue label of each segment in the plurality of segments.

In some embodiments, the boundary mesh or the mesh patch corresponding to each tissue may have the tissue label of the tissue. In such cases, if the ray intersects the mesh patch, a tissue label of an intersection of the ray with a mesh patch may be determined based on the tissue label of the mesh patch. For example, an intersection of the ray with a mesh patch of the heart may have a tissue label corresponding to the heart. Further, the processing device 140 may determine the tissue label of each segment in the plurality of segments based on the tissue labels of the one or more intersections. For example, a tissue label of a start point and/or a tissue label of an end point of each segment may be determined as a tissue label of the segment. Merely by way of example, a segment passing through the heart may have a tissue label corresponding to the heart.

In 830, the processing device 140 may determine a plurality of sampling points along the ray.

In some embodiments, in the volume rendering operation, a ray may be transmitted from each pixel on the screen based on camera parameters (e.g., a camera position). Further, a plurality of sampling points may be determined along a path of the ray passing through the volume data. Further, a color of the pixel corresponding to the ray may be determined by performing, based on the plurality of sampling points, a sampling operation on the volume data. For example, a brightness of each sampling point of the plurality of sampling points may be determined. And a brightness of the ray may be determined based on brightness of the plurality of sampling points. The brightness of the ray may be used to represent a color of a pixel corresponding to the ray on a rendered image. In some embodiments, the plurality of sampling points may be determined according to a fixed step or a random step along the ray. Merely by way of example, in a volume rendering operation based on a ray casting algorithm, the step between each two sampling points of the plurality of sampling points may be a fixed step determined based on a resolution of the volume data.

In 840, for each sampling point of the plurality of sampling points, the processing device 140 may determine, based on the tissue label of each segment in the plurality of segments, a tissue label of the sampling point.

In some embodiments, the processing device 140 may determine a segment where each sampling point of the plurality of sampling points is located. Further, the processing device 140 may determine the tissue label of the sampling point based on the tissue label of the segment. For example, the processing device 140 may determine the tissue label of the segment where the sampling point is located as the label of the sampling point.

In 850, the processing device 140 may determine whether each of the tissue labels of the plurality of sampling points is visible.

In some embodiments, a tissue label of each tissue in the one or more tissues may be set as visible or invisible in the rendering result. For example, the tissue label of a tissue of interest may be set to be visible and the tissue label of a tissue of no interest may be set to be invisible. In such cases, the processing device 140 may determine whether the tissue label of each sampling point is visible in the sampling operation of the volume rendering operation. Further, the processing device 140 may determine, based on a determination result of whether each of the tissue labels of the plurality of sampling points is visible, the volume rendering result of the tissue.

In 860, for each sampling point of the plurality of sampling points, in response to determining that the tissue label of the sampling point is invisible, the processing device 140 may skip a segment where the sampling point is located and proceed to a next segment.

In some embodiments, if the tissue label of the sampling point is invisible, the tissue label of the segment where the sampling point is located may be invisible. In such cases, there is no need to perform the sampling operation on the segment. The processing device 140 may skip the segment where the sampling point is located and perform the sampling operation on a next segment.

In 870, in response to determining that the tissue label of the sampling point is visible, the processing device 140 may determine, based on one or more rendering parameters corresponding to the tissue label of the sampling point, a contribution of the sampling point to a brightness of the ray.

In some embodiments, if the tissue label of the sampling point is visible, the tissue label of the segment where the sampling point is located may be visible, and the sampling operation may be performed on the segment. In some embodiments, for each sampling point with the visible tissue label on the ray, the processing device 140 may determine, based on the one or more rendering parameters corresponding to the tissue label, the brightness of the sample point using a lighting model. In some embodiments, the brightness of the sampling point may be used as the contribution of the sampling point to the brightness of the ray. The one or more rendering parameters may refer to parameters used to map data attributes (e.g., voxel values) of one or more voxels corresponding to the sampling point in the volume data to optical attributes (e.g., RGB values, the opacity, etc.) of the one or more voxels. Exemplary rendering parameters may include a color table, material parameters, or the like. In some embodiments, different tissue labels may correspond to different rendering parameters. For example, the heart and the blood vessels may correspond to different color tables or different material parameters.

Merely by way of example, the volume rendering operation performed based on a ray casting algorithm may be taken as an example for illustration. For each sampling point with the visible tissue label on the ray, a voxel value of the sampling point may be obtained by performing an interpolation operation based on voxel values of one or more voxels (e.g., eight voxels) near the sampling point. Further, a color table corresponding to the tissue label of the sampling point may be determined based on the tissue label of the sampling point. A color (i.e., a RGB value) and an opacity corresponding to the tissue label may be obtained according to the color table. A brightness of the ray at the sampling point may be determined, based on the color, the opacity, the material parameters, or the like, using the lighting model. The brightness may represent a color of the ray at the sampling point. Exemplary lighting models may include a Lambert lighting model, a Phong lighting model, a Blinn-Phong lighting model, or the like. For example, the brightness of the sampling point may be determined based on the Blinn-Phong lighting model in Equation (1):

$$\begin{aligned} I_{volume} &= I_{emission} + I_{BlinnPhong} \\ &= I_{emission} + I_{ambient} + I_{diffuse} + I_{specular} \\ &= k_e I_e + k_a M_a I_a + k_d M_d I_d \langle l^{\circ} n \rangle + k_s M_s I_s \langle h^{\circ} n \rangle^n, \end{aligned} \tag{1}$$

where $I_{volume}$ denotes a brightness of the illumination at the sampling point, $I_{emission}$ denotes a brightness of a self-illuminated light of the volume data; $I_{ambient}$ denotes a brightness of the ambient light, $k_a$ denotes a coefficient of the ambient light(s), $M_a$ denotes a material color corresponding to the ambient light, la denotes an intensity corresponding to the ambient light; $I_{diffuse}$ denotes a brightness of a diffused light, $k_d$ denotes a coefficient of the diffused light, Md denotes a material color corresponding to the diffused light, $l_d$ denotes an intensity corresponding to diffused light, <l°n> denotes a result of dot product between a light source direction and a normal direction; $I_{specular}$ denotes a brightness of a specular light, $k_s$ denotes a coefficient of the specular light coefficient, $M_s$ denotes a material color corresponding to the specular light, $I_s$ denotes an intensity corresponding to the specular light, h denotes a middle direction between the light source direction and a sight direction of the ray, <h°n> denotes a result of dot product between h and the normal direction, n denotes a glossiness in the material parameters. In Equation (1), $k_a$, $k_d$, and $k_s$ may be material parameters corresponding to the tissue label, $M_a$ and $M_d$ may be the colors obtained according to the color table.

In some embodiments, if a brightness corresponding to a sampling point located at a boundary of a tissue is determined, a normal of the boundary where the sampling point is located may be used as a normal of the sampling point. The normal of the boundary may be determined based on a gradient of the volume data. However, due to volumetric effect and other reason(s), the gradient of the volume data may be inconsistent with the normal of the boundary at a certain boundary, which may result in problems such as uneven illumination at the boundary and insufficient smoothness of the boundary of the tissue determined based on the normal of the boundary. In some embodiments, if the brightness of the sampling point is determined based on the boundary mesh, and the sampling point is close to the boundary mesh, a normal of the boundary mesh (e.g., a normal of a mesh patch intersecting with the ray) may be used as a normal of the sampling point instead of using the gradient of the volume data as the normal of the sampling point, which may reduce the problems such as uneven illumination at the boundary and insufficient smoothness of the boundary caused by the inconsistency between the gradient of the volume data and the normal of the boundary, thereby improving the quality of the rendered image.

In 880, the processing device 140 may determine the brightness of the ray based on a plurality of contributions of the plurality of sampling points.

In some embodiments, the processing device 140 may determine the brightness of the ray based on a plurality of contributions of the plurality of sampling points with visible tissue labels to the ray. For example, the brightness of the ray may be obtained by integrating the brightness of the sampling points with the visible tissue label along the ray. The brightness may be used to represent a color of the pixel corresponding to the ray in the rendered image. For example, a superimposed color or a superimposed opacity of the ray at a current sampling point may be determined based on the brightness (or referred to as a color) or the opacity of the sampling point. The superimposed color obtained by traversing the plurality of sampling points may be used as the brightness of the ray. Merely by way of example, the superimposed color at the current sampling point may be a superimposed value of the color of each previous sampling point with the visible tissue label on the ray and the color of the current sampling point, and the superimposed opacity at the current sampling point may be a superimposed value of the opacity of each previous sampling point with the visible tissue label on the ray and the opacity of the current sampling point. Merely by way of example, the superimposed color of the current sampling point may be determined based on Equation (2), and the superimposed opacity of the current sampling point may be calculated based on Equation (3):

$$C'_{dst} = C''_{dst} + (1 - \alpha''_{dst}) C_{src}, \tag{2}$$

$$\alpha'_{dst} = \alpha''_{dst} + (1 - \alpha''_{dst}) \alpha_{src}, \tag{3}$$

where $$C'_{dst}$$

denotes a superimposed color of the ray at the current sampling point, $$C''_{dst}$$

denotes a superimposed color of the ray at a previous sampling point with the visible tissue label.

$$\alpha''_{dst}$$

denotes a superimposed opacity of the ray at the previous visible sampling point, $C_{src}$ denotes a color corresponding to the current sampling point obtained based on Equation (1) above;

$$\alpha'_{dst}$$

denotes a superimposed opacity of the ray at the current sampling point, $\alpha_{src}$ denotes an opacity corresponding to the current sampling point obtained according to the color table. According to Equation (2) and Equation (3), the superimposed color and superimposed opacity at each sampling point along the ray may be determined. In some embodiments, an initial superimposed color and an initial superimposed opacity may be 0.

According to the above operations, the brightness and opacity of each sampling point with the visible tissue label may be determined and integrated along the ray such that the superimposed color and superimposed opacity of the ray at each sampling point may be obtained until the ray exceeds the range of the volume data. A final superimposed color may be used as the color (also referred to as a brightness) of the pixel corresponding to the ray in the volume rendering result. In such cases, for each pixel on the screen, the superimposed color of a ray passing through the pixel may be obtained by integrating the color of each sampling point with the visible tissue label along the ray such that the brightness of the ray can be determined. In some embodiments, the processing device 140 may display, based on the brightness of the ray, the volume rendering result of the tissue. In some embodiments, the volume rendering result may be displayed as a rendered image on the screen, and the brightness of each ray obtained in the volume rendering operation may be the color of each pixel in the rendered image.

In some embodiments, the ray may have a plurality of intersections with the tissue along the ray. For example, in the blood vessels in FIG. 9B, the ray may sequentially pass through a blood vessel 910 and a blood vessel 920. The ray may have two intersections with blood vessel 910 and two intersections with blood vessel 920 along the ray. In some embodiments, to determine the brightness of the ray, the volume rendering operation may be performed on a portion of the plurality of intersections. For example, two intersections closest to a starting point of the ray (e.g., a camera position or the pixel on the screen) may be determined based on the one or more boundary meshes of the tissue. Further, a segment between the two intersections and one or more sampling points on the segment may be determined. For each sampling point on the segment, a tissue label of the sampling point may be determined based on the tissue label of the boundary mesh. Merely by way of example, the boundary mesh of the blood vessel 910 and the two intersections of the ray and the boundary mesh may be determined. Further, based on the tissue label of the boundary mesh, the tissue label of the one or more sampling points between the two intersections may be determined. Further, the brightness of each sampling point may be determined. In some embodiments, for other sampling points on the ray, the tissue label of each of the other sampling points may be directly determined based on one or more voxels adjacent to the sampling point. For example, for the blood vessel 920, the tissue label of each sampling point may be determined based on the tissue labels of one or more voxels adjacent to the sampling point instead of the tissue label of the boundary mesh of the blood vessel 920. In such cases, on the one hand, the volume rendering operation may be performed on the tissues close to the screen based on the boundary mesh, which may improve the quality of the volume rendering result; on the other hand, the volume rendering operation may be performed on the following sampling points (e.g., the sampling point(s) with the visible tissue label(s)) of the two intersections closest to the starting point of the ray based on the tissue labels of the one or more voxels adjacent to the sampling point(s), which may reduce the amount of data and computation, thereby improving the efficiency of the volume rendering operation.

It should be noted that the above description for the process 800 is merely provided for the purposes of illustration, and not intended to limit the scope of the present disclosure. For persons having ordinary skills in the art, multiple variations and modifications may be made under the teachings of the present disclosure. In some embodiments, the operations of the process 800 are not sequential. In some embodiments, the process 800 may include one or more additional operations, or one or more operations of the process 800 may be omitted. In some embodiments, at least two operations in the process 800 may be incorporated into an operation for implementation or one operation in the process 800 may be divided into two operations. For example, the process 800 may include the operation of displaying the volume rendering result.

Figure 9A:
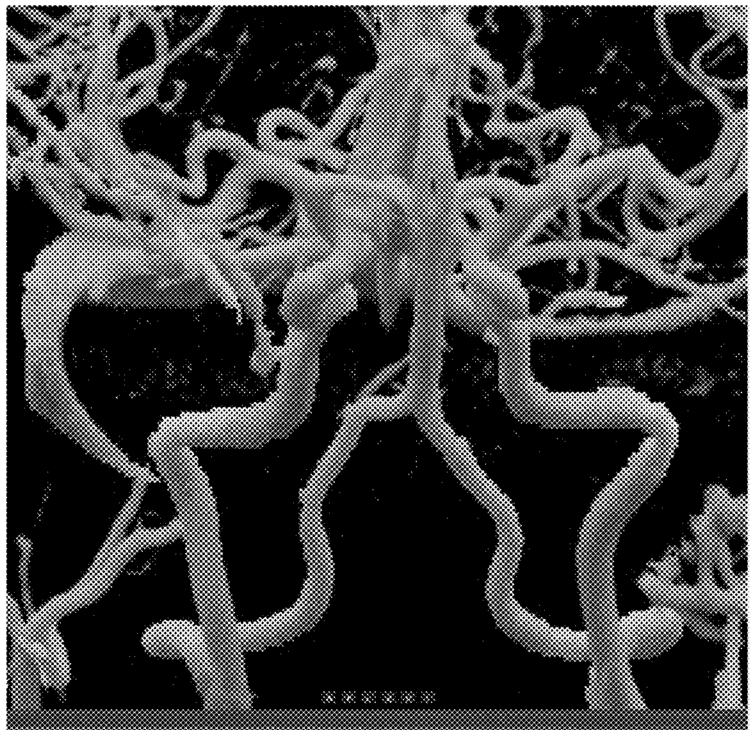
FIG. 9A and FIG. 9B are schematic diagrams illustrating exemplary rendered images according to some embodiments of the present disclosure.
Figure 9B:
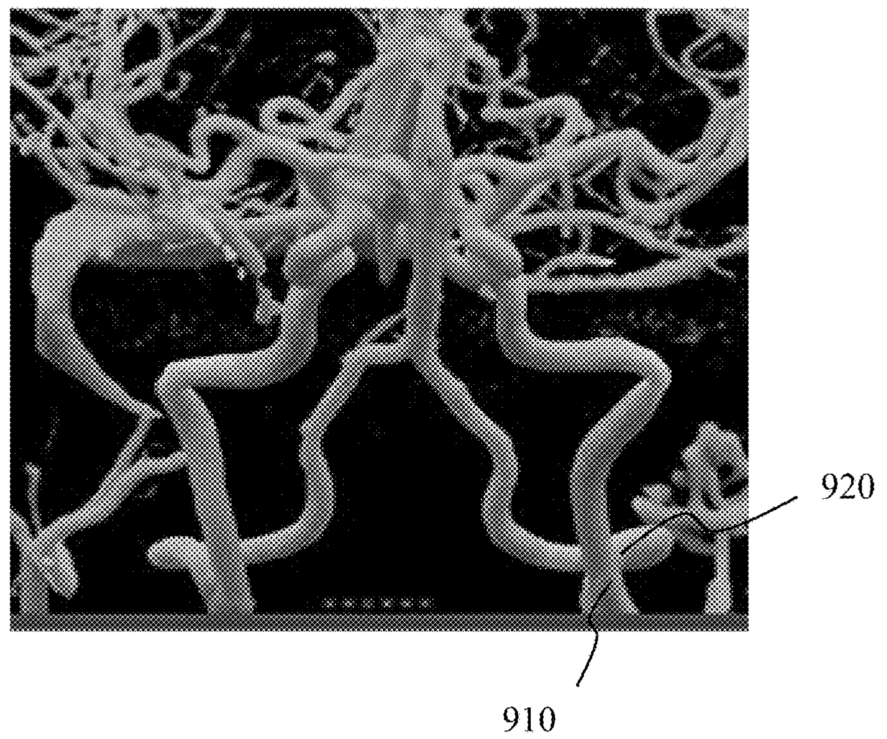

FIG. 9A and FIG. 9B are schematic diagrams illustrating exemplary rendered images according to some embodiments of the present disclosure. The image shown in FIG. 9A is an image obtained by performing a volume rendering operation based on a nearest neighbor interpolation manner. The image shown in FIG. 9B is an image obtained by performing a volume rendering operation based on one or more boundary meshes according to some embodiments of the present disclosure. As shown in FIG. 9B, the rendered image generated according to the operations described in the embodiments of the present disclosure may provide improved boundary information of the tissue. For example, the boundaries of the blood vessels shown in FIG. 9A are not smooth enough and have serrations, while the boundaries of the blood vessels in FIG. 9B are more continuous and smoother.

The beneficial effects in the embodiments of the present discourse may include but are not limited to: (1) the volume rendering method may be used to perform a segmentation operation on the volume data and extract the one or more boundary meshes of one or more tissues based on a result of the segmentation operation. Further, a smoothing operation may be performed on the one or more boundary meshes. In such cases, more continuous and smoother boundary meshes may be obtained while retaining boundary characteristics between tissues. In the volume rendering operation, the boundary meshes after the smoothing operation may provide accurate tissue boundary information and improve the continuity and smoothness of the boundaries of the one or more tissues in the volume rendering result such that the volume rendering result are not affected by the resolution of the volume data, which may improve the quality of the volume rendering result and the efficiency of the volume rendering operation; (2) in a process for determining a brightness of a ray based on the one or more boundary meshes, a mesh normal of a boundary mesh may be used as a normal of a sampling point near the boundary mesh, which may eliminate or alleviate the problems such as uneven illumination at the boundary and insufficient smoothness of the boundary of the tissue in the rendered image caused by an inconsistency between the gradient of the volume data and the boundary normal, thereby improving the quality of the rendered image; (3) a BVH algorithm may be used to manage the one or more boundary meshes of the one or more tissues such that when determining the one or more intersections of the ray with at least one of the one or more boundary meshes, it is not necessary to determine whether there is an intersection between the ray and each mesh patch, which may reduce redundant calculations when the ray does not intersect with the mesh patch, thereby reducing the computational complexity and improving the computational speed of determining the one or more intersections of the ray with at least one of the one or more boundary meshes.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms “one embodiment,” “an embodiment,” and/or “some embodiments” mean that a particular feature, structure or characteristic described in connection with the embodiment is included in at least one embodiment of the present disclosure. Therefore, it is emphasized and should be appreciated that two or more references to “an embodiment” or “one embodiment” or “an alternative embodiment” in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a “unit,” “module,” or “system.” Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the “C” programming language, Visual Basic, Fortran 2103, Perl, COBOL 2102, PHP, ABAP, dynamic programming languages such as Python, Ruby and Groovy, or other programming languages. The program code may execute entirely on the user’s computer, partly on the user’s computer, as a stand-alone software package, partly on the user’s computer and partly on a remote computer or entirely on the remote computer or server. In the latter scenario, the remote computer may be connected to the user’s computer through any type of network, including a local region network (LAN) or a wide region network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term “about,” “approximate,” or “substantially.” For example, “about,” “approximate,” or “substantially” may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for volume rendering, implemented on a computing device having at least one storage device storing a set of instructions, and at least one processor in communication with the at least one storage device, the method comprising:

obtaining, based on volume data, one or more boundary meshes of one or more tissues;

for each ray in a volume rendering operation, determining one or more intersections of the ray with at least one of the one or more boundary meshes;

determining a tissue label for each of the one or more tissues as visible or invisible in a volume rendering result, each of the one or more boundary meshes having the tissue label of the corresponding tissue; wherein a tissue label of each of the one or more intersections is the same as the tissue label of the boundary mesh corresponding to the intersection;

determining, based on the one or more intersections, target sampling points on the ray, including:

determining, based on the one or more intersections, at least one segment on the ray, each segment being between two adjacent intersections of the one or more intersections, a tissue label of each segment being the same as the tissue label of the intersection corresponding to the segment;

determining a plurality of first sampling points on the at least segment, a tissue label of each first sampling point being the same as the tissue label of the segment where the first sampling point is located; and determining the target sampling points in the plurality of first sampling points with the tissue labels that are set as visible, wherein the first sampling points with the tissue labels that are set as invisible are not involved in the determining of the brightness of the ray;

determining a brightness of each target sampling point based on one or more rendering parameters corresponding to the target sampling point and a normal of the target sampling point, wherein in response to determining that the target sampling point is adjacent to the one or more boundary meshes, a normal of a mesh patch, intersecting with the ray, of the one or more boundary meshes is used as the normal of the target sampling point; and determining, based on the brightness of the target sampling points, a volume rendering result of at least one of the one or more tissues.

2. The method of claim 1, wherein the obtaining, based on volume data, one or more boundary meshes of one or more tissues includes:

determining the tissue label for each voxel by performing a segmentation operation on the volume data; and determining, based on the tissue label of the each voxel, a target boundary mesh, among the one or more boundary meshes, of a target tissue.

3. The method of claim 2, wherein the determining, based on the tissue label of the each voxel, a target boundary mesh includes:

performing, based on one or more tissue labels of the one or more tissues, a binarization operation on the volume data; and determining, based on a result of the binarization operation, the target boundary mesh of the target tissue.

4. The method of claim 3, wherein the determining, based on a result of the binarization operation, the target boundary mesh of the target tissue includes:

determining, based on at least one of a Marching Cube algorithm, a Simple Marching Cubes algorithm, a Cuberille algorithm, or a Delaunay algorithm, the target boundary mesh of the target tissue.

5. The method of claim 1, further comprising:

performing a smoothing operation on the at least one of the one or more boundary meshes.

6. The method of claim 1, wherein the at least one of the one or more boundary meshes includes a plurality of mesh patches, and the determining one or more intersections of the ray with at least one of the one or more boundary meshes includes:

traversing the plurality of mesh patches to determine one or more intersections of the ray with the plurality of mesh patches as the one or more intersections of the ray with the at least one of the one or more boundary meshes.

7. The method of claim 6, wherein the determining one or more intersections of the ray with at least one of the one or more boundary meshes further includes:

managing, based on a bounding volume hierarchy (BVH) algorithm, the at least one of the one or more boundary meshes.

8. The method of claim 7, wherein one or more parent nodes and one or more leaf nodes are configured in the BVH algorithm, each of the one or more parent nodes corresponding to a bounding box, and each of the one or more leaf nodes corresponding to one or more mesh patches of the plurality of mesh patches.

9. The method of claim 8, wherein the traversing the plurality of mesh patches includes:

for each parent node of the one or more parent nodes, determining whether the ray intersects with the parent node; and in response to determining that the ray intersects with the parent node, determining one or more intersections of the ray with one or more leaf nodes corresponding to the parent node as the one or more intersections of the ray with the plurality of mesh patches; or in response to determining that the ray does not intersect with the parent node, skipping the parent node and the one or more leaf nodes corresponding to the parent node.

10. The method of claim 1, wherein the determining, based on the brightness of the target sampling points, a volume rendering result of at least one of the one or more tissues includes:

for the each ray in the volume rendering operation, dividing, based on the one or more intersections, the ray into a plurality of segments;

determining the tissue label of each segment in the plurality of segments; and generating, based on the tissue label of each segment in the plurality of segments, the volume rendering result of the tissue.

11. The method of claim 10, wherein the generating, based on the tissue label of each segment in the plurality of segments, the volume rendering result of the tissue includes:

determining a plurality of sampling points along the ray;

for each sampling point of the plurality of sampling points, determining, based on the tissue label of each segment in the plurality of segments, a tissue label of the sampling point; and determining, based on the tissue labels of the plurality of sampling points, the volume rendering result of the tissue.

12. The method of claim 11, wherein the determining, based on the tissue labels of the plurality of sampling points, the volume rendering result of the tissue includes:

determining whether each of the tissue labels of the plurality of sampling points is visible; and determining, based on a determination result of whether each of the tissue labels of the plurality of sampling points is visible, the volume rendering result of the tissue.

13. The method of claim 12, wherein the determining, based on a determination result of whether each of the tissue labels of the plurality of sampling points is visible, the volume rendering result of the tissue includes:

for each sampling point of the plurality of sampling points, in response to determining that the tissue label of the sampling point is invisible, skipping a segment where the sampling point is located and proceeding to a next segment;

in response to determining that the tissue label of the sampling point is visible, determining, based on one or more rendering parameters corresponding to the tissue label of the sampling point, a contribution of the sampling point to a brightness of the ray; and determining, based on a plurality of contributions of the plurality of sampling points, the brightness of the ray.

14. The method of claim 13, further comprising:

displaying, based on the brightness of the ray, the volume rendering result of the tissue.

15. The method of claim 1, wherein the determining one or more intersections of the ray with at least one of the one or more boundary meshes includes:

constructing a distance field of the at least one of the one or more boundary meshes, for any point in the volume data, the distance field including a shortest distance from the point to the at least one of the one or more boundary meshes; and determining the one or more intersections of the ray with the at least one of the one or more boundary meshes based on the distance field.

16. The method of claim 15, wherein the determining the one or more intersections of the ray with the at least one of the one or more boundary meshes based on the distance field includes:

determining a plurality of points by marching along the ray;

determining a shortest distance from each point of the plurality of points on the ray to the at least one of the one or more boundary meshes based on the distance field;

determining whether the ray intersects the at least one of the one or more boundary meshes based on the shortest distance of each point along the ray; and in response to determining that the ray intersects the at least one of the one or more boundary meshes, determining the one or more intersections of the ray with the at least one of the one or more boundary meshes.

17. The method of claim 1, wherein the at least one segment is one segment between two intersections, among the one or more intersections, closest to a starting point of the ray; and the method further comprises:

determining a plurality of second sampling points on a portion of the ray that is out of the segment between the two intersections;

for each second sampling point, determining the tissue label of the tissue corresponding to one or more voxels adjacent to the second sampling point as a tissue label of the second sampling point;

determining the brightness of the ray based on the second sampling points with the tissue labels that are set as visible, wherein the second sampling points with the tissue labels that are set as invisible are not involved in the determining of the brightness of the ray.

18. A system for volume rendering, comprising:

at least one storage medium including a set of instructions; and at least one processor in communication with the at least one storage medium, wherein when executing the set of instructions, the at least one processor is directed to cause the system to:

obtain, based on volume data, one or more boundary meshes of one or more tissues;

for each ray in a volume rendering operation, determine one or more intersections of the ray with at least one of the one or more boundary meshes;

determining a tissue label for each of the one or more tissues as visible or invisible in a volume rendering result, each of the one or more boundary meshes having the tissue label of the corresponding tissue; wherein a tissue label of each of the one or more intersections is the same as the tissue label of the boundary mesh corresponding to the intersection;

determining, based on the one or more intersections, target sampling points on the ray, including:

determining, based on the one or more intersections, at least one segment on the ray, each segment being between two adjacent intersections of the one or more intersections, a tissue label of each segment being the same as the tissue label of the intersection corresponding to the segment;

determining a plurality of first sampling points on the at least segment, a tissue label of each first sampling point being the same as the tissue label of the segment where the first sampling point is located; and determining the target sampling points in the plurality of first sampling points with the tissue labels that are set as visible wherein the first sampling points with the tissue labels that are set as invisible are not involved in the determining of the brightness of the ray;

determining a brightness of each target sampling point based on one or more rendering parameters corresponding to the target sampling point and a normal of the target sampling point, wherein in response to determining that the target sampling point is adjacent to the one or more boundary meshes, a normal of a mesh patch, intersecting with the ray, of the one or more boundary meshes is used as the normal of the target sampling point; and determine, based on the brightness of the target sampling points, a volume rendering result of at least one of the one or more tissues.

19. A non-transitory computer readable medium, comprising executable instructions that, when executed by at least one processor, direct the at least one processor to perform a method for volume rendering, the method comprising:

obtaining, based on volume data, one or more boundary meshes of one or more tissues;

for each ray in a volume rendering operation, determining one or more intersections of the ray with at least one of the one or more boundary meshes;

determining a tissue label for each of the one or more tissues as visible or invisible in a volume rendering result, each of the one or more boundary meshes having the tissue label of the corresponding tissue; wherein a tissue label of each of the one or more intersections is the same as the tissue label of the boundary mesh corresponding to the intersection;

determining, based on the one or more intersections, target sampling points on the ray, including:

determining, based on the one or more intersections, at least one segment on the ray, each segment being between two adjacent intersections of the one or more intersections, a tissue label of each segment being the same as the tissue label of the intersection corresponding to the segment;

determining a plurality of first sampling points on the at least segment, a tissue label of each first sampling point being the same as the tissue label of the segment where the first sampling point is located; and determining the target sampling points in the plurality of first sampling points with the tissue labels that are set as visible wherein the first sampling points with the tissue labels that are set as invisible are not involved in the determining of the brightness of the ray;

determining a brightness of each target sampling point based on one or more rendering parameters corresponding to the target sampling point and a normal of the target sampling point, wherein in response to determining that the target sampling point is adjacent to the one or more boundary meshes, a normal of a mesh patch, intersecting with the ray, of the one or more boundary meshes is used as the normal of the target sampling point; and determining, based on the brightness of the target sampling points, a volume rendering result of at least one of the one or more tissues.

* * * * *